Feb. 16, 1965 J. R. MITTLEIDER Plant Pat. 2,480
DIANTHUS PLANT
Filed Sept. 23, 1963
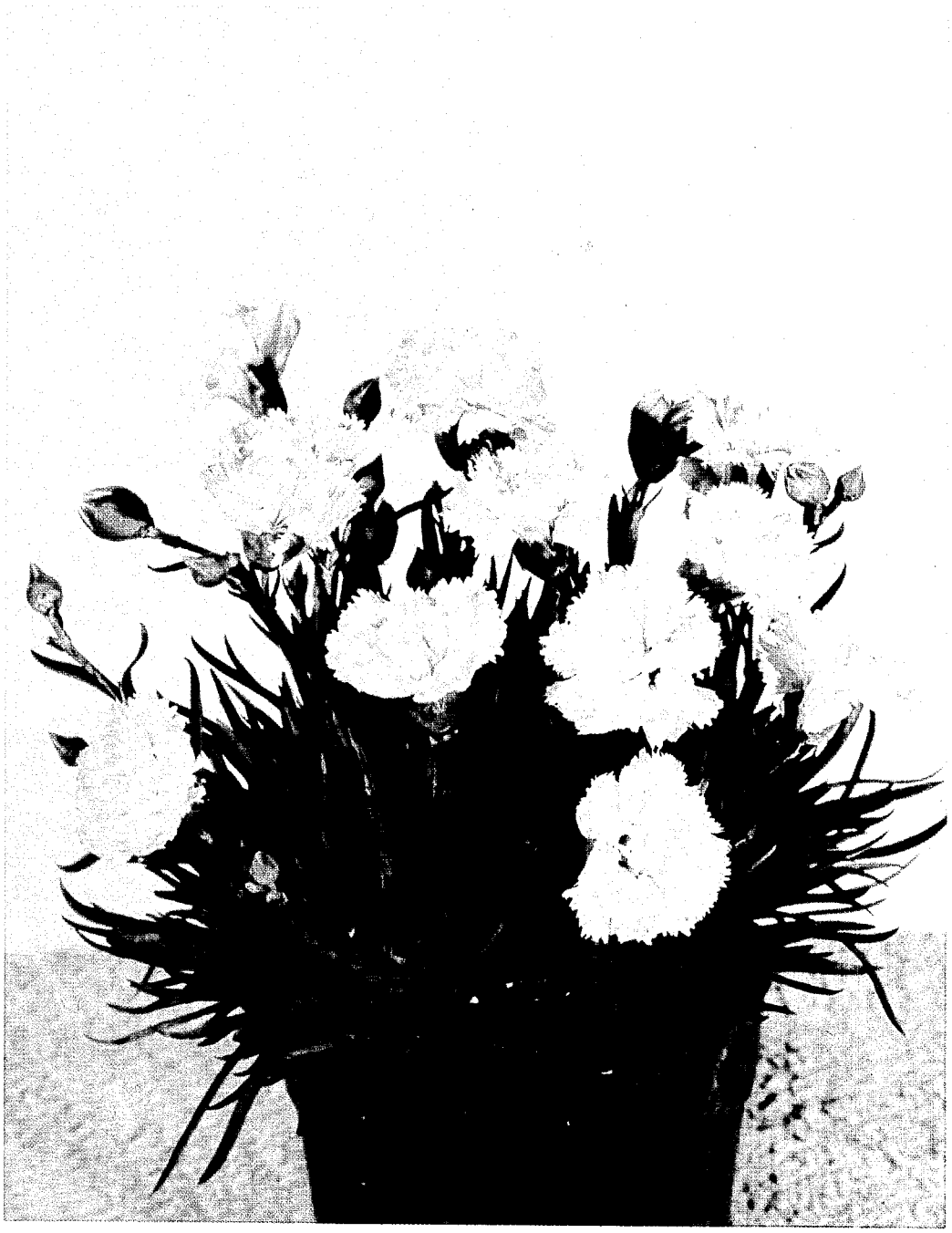
INVENTOR
JACOB R. MITTLEIDER
BY Herbert E. Kidder
AGENT United States Patent Office Plant Pat. 2,480
Patented Feb. 16, 1965

2,480
DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,964
1 Claim. (Cl. Plt.—70)

The present invention relates to a new and distinct variety of dianthus plant, which is characterized particularly by a low growing, compact, densely tufted plant bearing numerous large, very double ruffled flowers of a creamy white color, and very fragrant with spicy, carnation-like fragrance.

The new and different plant variety is the result of an extensive breeding program at my nursery in Loma Linda, California, seeking new varieties of dianthus that would be especially suitable for mass plantings or edgings, without the necessity of staking the plants. The characteristics sought were: (1) carnation foliage, (2) ever-blooming habit, (3) compactness, (4) fragrance, (5) large blooms, (6) strong stems, (7) hardiness and disease resistance, (8) pleasing new colors.

The present variety is the result of a two step breeding operation, in which Dianthus Old Spice (Plant Patent No. 499) was pollinated with pollen from Dianthus Rose Bowl (Plant Patent No. 2,034). Seedlings from the first cross, selected for plant foliage, were then pollinated with the pollen of a picotee carnation seedling unnamed and unpattented having a double white blossom with a marginal band of pink. The present plant variety is one of 600 seedlings from this second cross, which was outstanding in every respect, with compact, densely tufted, low growing foliage, and masses of large, very double, heavily scented flowers of creamy white.

The original reproduction of the plant by cuttings was carried out in the experimental section of my nursery at Loma Linda, California. Asexual reproduction of my new variety by cuttings, as performed by me at the nursery, shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Compact, growing to a height of three to four inches.

*Growing habit.*—Densely tufted.

*Blooming habit.*—Floriferous, flowering evenly over the entire plant with blossoms ranging from 2 inches to 2¼ inches in diameter, and ranging in number from 3 or 4 on one year old plants grown in three-inch pots, up to 20 or more on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs in springtime, with heaviest bloom around Easter. Scattered blooming during most of the rest of the year except for August and September, when blooming ceases and vegetative growth takes place.

*Foliage size.*—Maximum size of mature leaves on thrifty young plants is approximately 3 inches in length, by three-sixteenths of an inch in width.

*Quantity.*—Abundant.

*Shape.*—Lanceolate—or grass-like.

*Color.*—Growing under good conditions, the color of mature leaves is a deep true green, corresponding almost exactly to Aspen Green (Plates 31–C–6 in Maerz and Paul's Color Dictionary).

*Texture.*—Glaucous.

Flower:

*Size.*—The maximum size is about 2 to 2¼ inches in diameter, by 1 inch high.

*Borne.*—At the end of the stems.

*Stem.*—Stiff and upright, approximately 4 to 6 inches in length.

*Petalage.*—Very double.

*Color.*—The flower is almost pure white, with a faintly creamy cast (Plate 10–B–1, Maerz and Paul, Oyster White).

*Petals.*—Of obovate form with regularly crenate margins. The size of the individual petals is about 1¼ inches in length, by ¾ inch in width.

*Fragrance.*—Heavily scented with spicy, carnation-like fragrance.

*Calyx.*—Spreading at the tip, with acuminate teeth, and approximately ¾ inch in length.

Compared to other well-known dianthus plants, this new variety is distinguished by its low-growing, compact form and masses of large, very double, white flowers that are heavily scented with spicy, carnation-like fragrance.

I claim:

A new and distinct variety of dianthus plant, substantially as shown and described herein, characterized particularly by its floriferous blooming habit, low-growing, compact, densely tufted plant form, usually not exceeding three to four inches in height, and bearing many large, very double, ruffled flowers of almost pure white, with a slightly creamy cast, said flowers being heavily scented with carnation-like fragrance, and being borne on the ends of stiff, upright stems approximately 4 to 6 inches in height.

No references cited.